(12) United States Patent  (10) Patent No.: US 8,894,716 B2
McMahon et al.  (45) Date of Patent: Nov. 25, 2014

(54) METHOD OF MAPPING FEMORAL HEAD FOR ACETABULAR PROSTHESIS ALIGNMENT

(71) Applicant: Smith & Nephew, Inc., Memphis, TN (US)

(72) Inventors: Stephen McMahon, Victoria (AU); Charles Wayne Allen, Southaven, MS (US); David C. Kelman, Collierville, TN (US)

(73) Assignee: Smith & Nephew, Inc., Memphis, TN (US)

( * ) Notice: Subject to any disclaimer, the term of this patent is extended or adjusted under 35 U.S.C. 154(b) by 0 days.

(21) Appl. No.: 13/935,091

(22) Filed: Jul. 3, 2013

(65) Prior Publication Data

US 2014/0018932 A1  Jan. 16, 2014

Related U.S. Application Data

(62) Division of application No. 12/919,104, filed as application No. PCT/US2009/035113 on Feb. 25, 2009, now Pat. No. 8,491,664.

(60) Provisional application No. 61/031,230, filed on Feb. 25, 2008.

(51) Int. Cl.
*A61F 2/32* (2006.01)
*A61F 2/34* (2006.01)
*A61F 2/36* (2006.01)
*A61F 2/46* (2006.01)
*A61B 19/00* (2006.01)
*A61F 2/30* (2006.01)

(52) U.S. Cl.
CPC ............... *A61F 2/34* (2013.01); *A61F 2/3609* (2013.01); *A61B 2019/5204* (2013.01); *A61B 2019/521* (2013.01); *A61B 2019/5206* (2013.01); *A61B 2019/5437* (2013.01); *A61F 2002/365* (2013.01); *A61B 2019/5445* (2013.01); *A61F 2250/0097* (2013.01); *A61B 19/5202* (2013.01); *A61B 2019/446* (2013.01); *A61B 19/54* (2013.01); *A61F 2002/30617* (2013.01); *A61B 2019/5441* (2013.01); *A61F 2/4684* (2013.01); *A61F 2002/4696* (2013.01); *Y10S 623/914* (2013.01)
USPC .................... 623/22.11; 623/22.15; 623/22.4; 623/23.42; 623/914

(58) Field of Classification Search
USPC .......... 623/19.11–19.14, 22.11, 22.12, 22.15, 623/22.4, 22.42, 23.42, 914; 606/89, 102
See application file for complete search history.

(56) References Cited

U.S. PATENT DOCUMENTS 5,507,824 A  4/1996 Lennox
6,120,540 A  9/2000 Apple et al.
(Continued)

OTHER PUBLICATIONS

International Search Report issued from European Patent Office, dated Aug. 5, 2009, regarding PCT/US2009/035113 (4 pages).

*Primary Examiner* — David Isabella
*Assistant Examiner* — Randy Shay
(74) *Attorney, Agent, or Firm* — Krieg DeVault LLP

(57) ABSTRACT

A method of orienting a femoral head member of an implant relative to an acetabular member positioned in the acetabulum including implanting a femoral stem of an implant within an intramedullary canal of a femur, inserting an acetabular member in the acetabulum, positioning a femoral head member of the implant at least partially in the acetabular member with the femoral head member including a curved articulating surface and a plurality of indicia on the curved articulating surface, and orienting the femoral head member relative to the acetabular member and generally aligning one of the indicia on the curved articulating surface with an alignment feature of the acetabular member to signify an orientation of the femoral head member relative to the acetabular member.

25 Claims, 13 Drawing Sheets

(56) References Cited

U.S. PATENT DOCUMENTS

| | | |
|---|---|---|
| 7,662,156 B2 | 2/2010 | Carson |
| 2001/0053935 A1 | 12/2001 | Hartdegen et al. |
| 2004/0122439 A1 | 6/2004 | Dwyer et al. |
| 2005/0004680 A1 | 1/2005 | Saladino et al. |
| 2005/0177244 A1 | 8/2005 | Steinberg |
| 2005/0197708 A1 | 9/2005 | Stone et al. |
| 2006/0058886 A1 | 3/2006 | Wozencroft |
| 2006/0259148 A1 | 11/2006 | Bar-Ziv |
| 2007/0179506 A1 | 8/2007 | Hoag et al. |
| 2008/0058951 A1 | 3/2008 | Saladino et al. |
| 2011/0060418 A1* | 3/2011 | Bailey et al. ............... 623/22.42 |

* cited by examiner

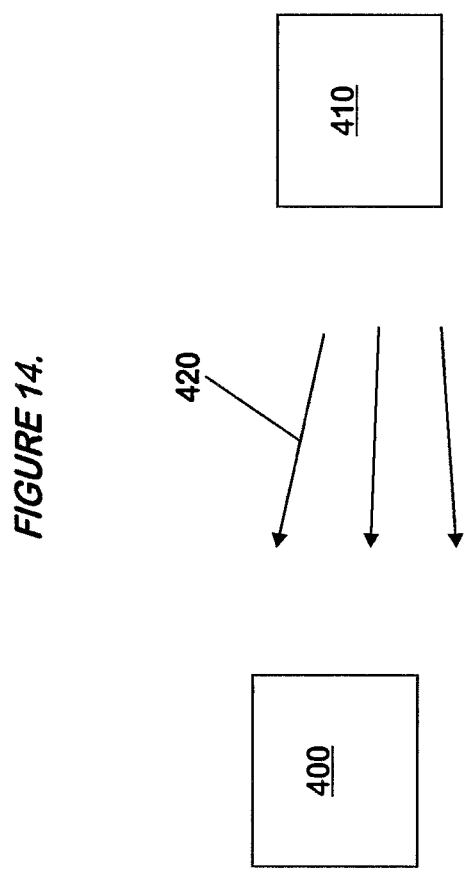

METHOD OF MAPPING FEMORAL HEAD FOR ACETABULAR PROSTHESIS ALIGNMENT

CROSS-REFERENCE TO RELATED APPLICATIONS

This application is a divisional of U.S. patent application Ser. No. 12/919,104 filed on Dec. 14, 2010, which is a U.S. National Phase filing of International Application No. PCT/US2009/035113 filed on Feb. 25, 2009, which claims the benefit of U.S. Provisional Application No. 61/031,230 filed on Feb. 25, 2008. The contents of each of these applications is incorporated herein by reference in its entirety.

BACKGROUND

1. Field

The present invention relates generally to systems and methods of implanting a hip prosthesis and more particularly to a system and method of determining prosthesis orientation using indicia.

2. Related Art

Trialing during prosthesis implantation is generally essential in joint arthroplasty. Trialing steps ensure proper placement and function as well as assess range of motion and stability. In some cases, for example, in hip arthroplasty, an acetabular shell component needs to be implanted before trialing can begin. Likewise, other instances such as in knee arthroplasty, a tibial tray component needs to be implanted before trialing can begin.

In total hip arthroplasty, an acetabulum is normally prepared by reaming or other methods, and may require the use of cages or augments in cases of significant bone loss, degeneration, or deformity. An appropriately sized acetabular shell component is impacted, cemented, screwed, or otherwise affixed to a prepared acetabulum and a trial insert liner is attached. A femoral component which articulates with the trial insert liner is provided to the femur, and trial reduction begins. In some cases such as hip resurfacing, a trial liner may be eliminated.

Correct orientation of an acetabular shell component may differ between patients. However, it has generally been accepted that for a population majority, the longitudinal apex axis of a properly aligned acetabular shell component is generally inclined between about 40 and 50 degrees in abduction, normally about 45 degrees in abduction, and between about 20 and 30 degrees in anteversion, normally about 25 degrees in anteversion. Correct orientation of a femoral neck component may differ between patients. However, it has generally been accepted that for a population majority, a properly aligned femoral neck is generally inclined between about 35 and 45 degrees in abduction, normally about 41 degrees in abduction (i.e., 41 degrees above horizontal), and between about 10 and 20 degrees in anteversion, normally about 15 degrees in anteversion.

Due to the nature of hip arthroplasty, it is sometimes difficult to verify correct placement of an installed acetabular shell component intraoperatively. If an acetabular shell is misaligned prior to impacting, cementing, screwing, or otherwise affixing it to a prepared acetabulum, any subsequent trialing procedures and/or final implantation of the prosthesis may be compromised. Misalignment of an acetabular shell component may reduce articulation surface area, thereby adversely affecting postoperative performance, function, wear rate, range of motion, and joint stability.

Therefore, it is an object of some embodiments of the present invention to provide a simple and effective way to reduce the occurrence of misaligned acetabular components intraoperatively.

Conventionally, acetabular shell component alignment has been addressed intraoperatively using fluoroscopy and crude positioning instruments. These methods, while effective, require additional resources, personnel, additional instruments, and/or expensive machinery.

To this end, a surgeon may use fluoroscopic means to visually determine any gross misalignments during surgery. However, precise orientation angles of the acetabular shell component cannot be readily determined from fluoroscopic imaging. Alternatively, a surgeon may orient an impactor handle such that it is in longitudinal alignment with a corner of the operating room in order to achieve an approximate insertion angle of 45 degrees abduction and 25 degrees anteversion. Even more alternatively, some orthopaedic manufacturers provide alignment guides which may be used with impactor handles during acetabular shell component installation. Such alignment guides generally comprise what is referred in the art as an "X-bar," "T-bar" or the like. A bar in the shape of an "X" protrudes from an impactor configured to install an acetabular shell component. The bar is attached to the impactor at predetermined orientation angle. With a patient lying in a predetermined position, the impactor is oriented such that the X-bar is parallel to the ceiling, floor, and/or table, and/or such that each extension of the "X" points to a corner of the square operating room. These methods, while effective, do not provide a finely calibrated visual feel-good device to a surgeon.

Indicia have been used on femoral heads to indicate a particular orthopaedic manufacturer, size, offset, or product SKU number. However, most indicia are generally found in the lip area or at the bottom of a tapered recess within the femoral heads and not located on an articulating surface.

Femoral head trial components of the prior art sometimes comprise a solid color indicative of a particular size or offset for a particular trial femoral head component. However, it is believed that such indicia are not configured to determine a spatial orientation of an acetabular shell component. Nor do such indicia comprise multiple colors on a single trial femoral head component.

U.S. Pat. No. 4,475,549 to Oh discloses an acetabular cup positioner of the prior art which utilizes a plurality of bar projections on an acetabular shell component impactor, the plurality of projections being configured for orientation purposes.

In U.S. Pat. No. 4,632,111 to Roche, a means for orientating an acetabular shell component comprises two threaded holes (66) and a threaded rod (64) with indicator ends (62). The rod (64), when placed in one of the holes (66), assists with positioning an acetabular shell component in a proper abduction angle. The rod (64), when placed in another of the holes (66), assists with positioning an acetabular shell component in a proper anteversion angle.

U.S. Pat. No. 4,305,394 to Bertuch, Jr., U.S. Des. Pat. No. D331,461 to Lester, and U.S. Pat. No. 5,364,403 to Petersen et al., further disclose prior art methods for positioning an acetabular shell component and associated apparatus.

In FIG. 49 of U.S. Published Patent Application US2007/0123908 published on May 31, 2007, and assigned Ser. No. 11/541,184, there is described an instrument which may include indicia or marks that can assist in the proper angular orientation of the modular components.

U.S. Published Patent Applications US2004/0122439 published on Jun. 24, 2004, and assigned Ser. No. 10/327,187 and US2004/0122440 published on Jun. 24, 2004, and assigned Ser. No. 10/327,527 describe placing indicia on first and second segments for determining the relative position of the first segment with respect to the second segment.

In U.S. Published Patent Application US2006/0058886 published on Mar. 16, 2006, and assigned Ser. No. 11/225,754, there is described an alignment trial system for a hip prosthesis comprising an interlocking trial femoral prosthesis and a trial acetabular cup prosthesis, wherein indicia is included to identify the engagement formation that is suitable for use in the right side and that which is suitable for use in the left side.

U.S. Published Patent Application US2004/0015238 published on Jan. 22, 2004, and assigned Ser. No. 10/346,316 describes providing a shroud for a femoral neck having indicia thereon for alignment purposes.

U.S. Pat. Nos. 5,002,581, 5,135,529, and 5,201,882 to Paxson et al. are drawn to a modular hip joint prosthesis comprising indicia adjacent to a connection portion, and a stem bearing one or more markings alignable with the indicia to indicate to a surgeon the relative rotational alignment between a trochanteral module and the stem.

U.S. Pat. No. 5,171,324 to Campana et al. discloses alignment indicia on a protruding lip of a femoral component for rotational alignment purposes.

U.S. Pat. No. 4,004,581 to Heimke et al. discloses indicia means for measuring the depth of penetration for a hip bone preparation tool.

All of the above-referenced U.S. patents and published U.S. patent applications are incorporated by reference as though fully described herein.

SUMMARY

According to some embodiments, there is provided a method of installing an acetabular component. The method includes the steps of: providing a femoral component having indicia thereon; providing an acetabular component; and, determining a position of the acetabular component using the indicia.

According to other embodiments, there is provided a method of manufacturing a set of surgical instruments, the method including the step of providing at least one femoral component adapted for articulation with an acetabular component, the femoral component comprising indicia thereon, the indicia relating to the spatial orientation of the acetabular component.

According to yet other embodiments, there is provided a method of trialing during hip arthroplasty, the method comprising the step of using indicia located on a femoral component to determine a spatial orientation of an acetabular component.

According to some embodiments, an apparatus for orienting a prosthetic femoral head relative to an acetabulum comprises a femoral stem and a femoral head member. The femoral stem is configured to be received within the intramedullary canal of a femur. The femoral head member is configured to couple to the femoral stem and further configured to be received in the acetabulum. The femoral head member further comprises an indicia configured to orient a relative position of the prosthetic femoral head to the acetabulum such that the indicia signifies proper relative position of the prosthetic femoral head in the acetabulum.

Another embodiment further comprises an acetabular component configured to be received in the acetabulum.

In yet another embodiment, at least one of the femoral head member and the femoral stem is a trial component.

According to other embodiments, the femoral head member further comprises a plurality of indicia, such that one of the plurality of indicia signifies proper relative position of the femoral head in the acetabulum and the other of the plurality of indicia signifies a measured amount of displacement from the proper relative position.

According to some embodiments, the measured amount of displacement is an angular measurement of relative rotation between the femoral head and the acetabulum.

In another embodiment, the femoral head member further comprises a plurality of indicia, such that one of the plurality of indicia signifies proper relative position of the femoral head in the acetabulum in a neutral position and the other of the plurality of indicia signifies a proper relative position as the position of the femoral stem is rotated through its range of motion relative to the acetabulum.

In yet another embodiment, the proper relative position is the proper orientation in abduction/adduction relative to the acetabulum.

Other embodiments include the proper relative position is the proper orientation in anteversion/retroversion relative to the acetabulum.

In another embodiment, the indicia is a line. The line may be latitudinally oriented on the femoral head member or longitudinally oriented on the femoral head member.

In yet another embodiment, the indicia is a portion of the surface of the femoral head member.

Alternatively, in an embodiment, the indicia is illuminated.

Another embodiment includes a method of orienting a prosthetic femoral head relative to an acetabulum. The method includes implanting a femoral stem within the intramedullary canal of a femur. Another step couples a femoral head member to the femoral stem. Yet another step orients the femoral head member relative to the acetabulum by positioning the prosthetic femoral head within the acetabulum. An indicia on the prosthetic femoral head is aligned and viewable when the prosthetic femoral head is properly positioned in the acetabulum.

In another embodiment, a step includes implanting an acetabular member such that the orienting step orients the femoral head member relative to the acetabular member.

Alternatively, an embodiment of the method may include reading an indicia signifying an improper position of the femoral head relative to the acetabular component. The indicia signifies an improper position is a measure of a displacement of the acetabular component from the proper position. A further step in the embodiment includes adjusting the position of the acetabular component in the acetabulum such that the amount of adjustment is relative to the measure of the displacement.

In yet another embodiment, the measure of displacement is a measure of an angular displacement.

Another embodiment includes the adjustment is an adjustment of the abduction/adduction of the acetabular component. Alternatively, the adjustment could be an adjustment of the anteversion/retroversion of the acetabular component.

In another embodiment, the reading step comprises reading an illuminated indicia.

Further areas of applicability will become apparent from the detailed description provided hereinafter. It should be understood that the detailed description and specific examples, while indicating certain embodiment of the invention, are intended for purposes of illustration only and are not intended to limit the scope of the invention.

Further features, aspects, and advantages of the present invention, as well as the structure and operation of various embodiments of the present invention, are described in detail below with reference to the accompanying drawings.

BRIEF DESCRIPTION OF THE DRAWINGS

The accompanying drawings, which are incorporated in and form a part of the specification, illustrate embodiments of the present invention and together with the description, serve to explain the principles of the invention. In the drawings:

FIG. 14 is a schematic diagram which illustrates a method for improving indicia visibility by external illumination according to some embodiments of the present invention.

DETAILED DESCRIPTION OF THE EMBODIMENTS

The Figures generally relate to geographically mapping a trial femoral head in order to assess the orientation of an acetabular shell component during trial reduction.

Figure 1A:
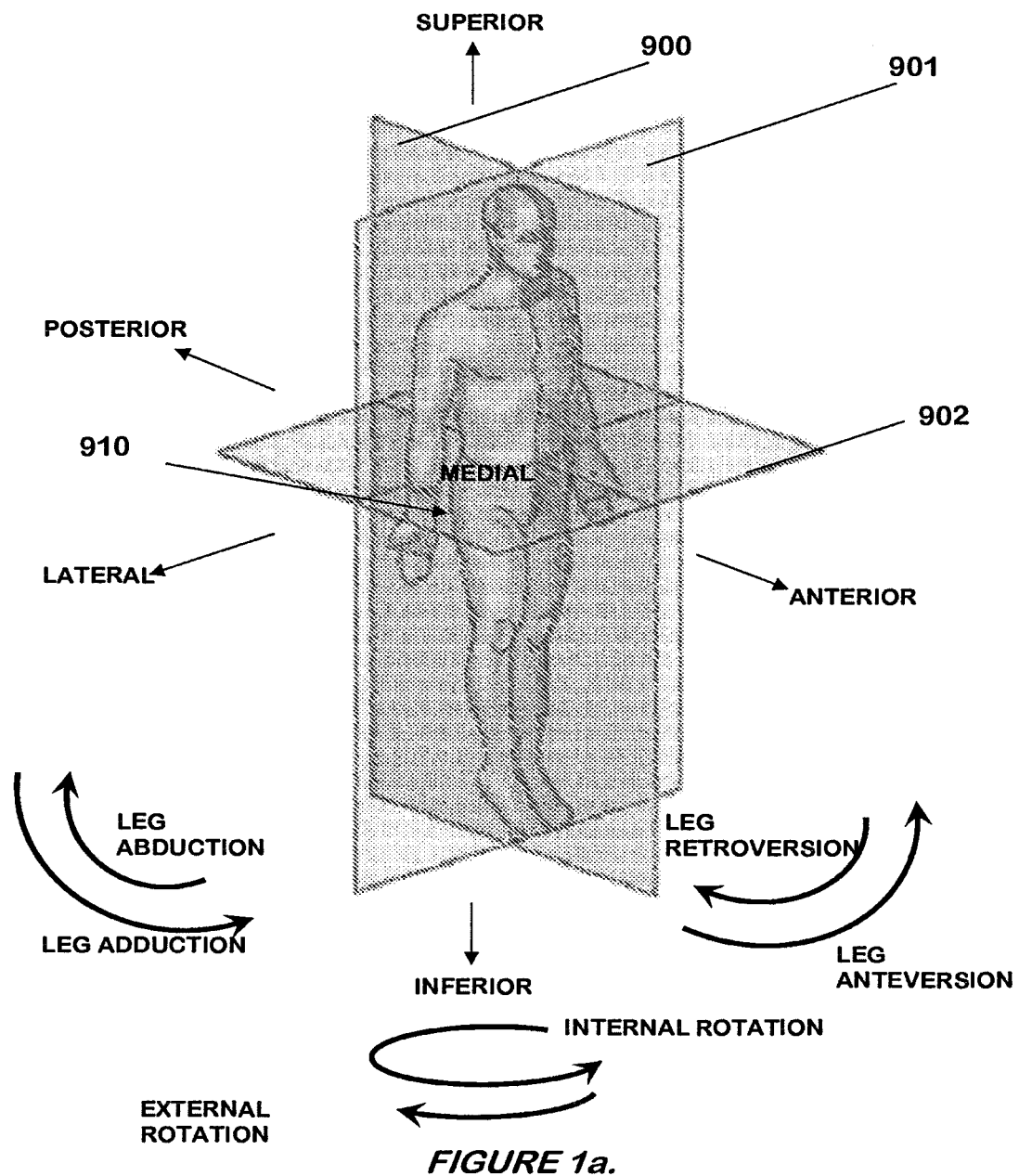
FIGS. 1a and 1b represent schematic diagrams of the relative terms used throughout this disclosure, with respect to human anatomy.
Figure 1B:
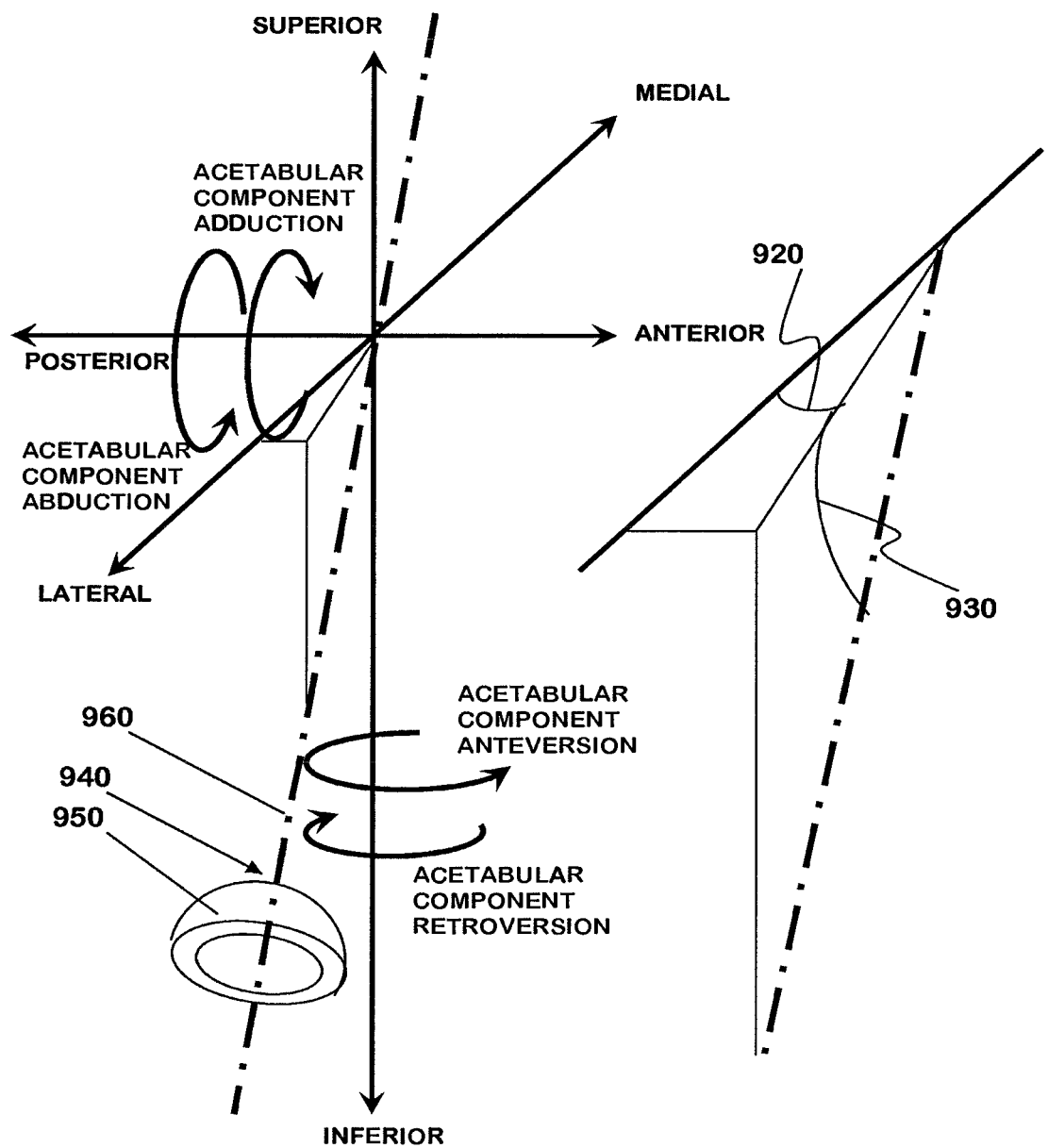

FIGS. 1a and 1b illustrate a right hip joint (910) and various directions of anatomical movement related to the human leg. FIG. 1a shows a hip joint (910), which allows a human leg to move anteriorly within a sagittal plane (900) during anteversion or posteriorly within the sagittal plane (900) in retroversion. Hip joint (910) also allows a human leg to move laterally within a coronal plane (901) during abduction and medially within the coronal plane (901) during adduction. Internal-external rotation may be enabled by twisting the leg about the superior inferior axis and within a transverse plane (902) while the leg is in full extension. However, rotation may be performed during any state of flexion, version, and/or abduction. FIG. 1b generally depicts a proper orientation of a natural acetabulum and correct installation of an acetabular component (950) relative to the axes of the body shown in FIG. 1a. Acetabular component (950) has a longitudinal axis (960) which runs through an apex (940) of the shell. In most normal cases, the longitudinal axis (960) forms an anteversion angle (920) of about 20-30 degrees with respect to the medial-lateral axis. In most normal cases the longitudinal axis (960) of the acetabular component (950) forms an abduction angle (930) if about 40-50 degrees with respect to the medial-lateral axis.

Figure 2:
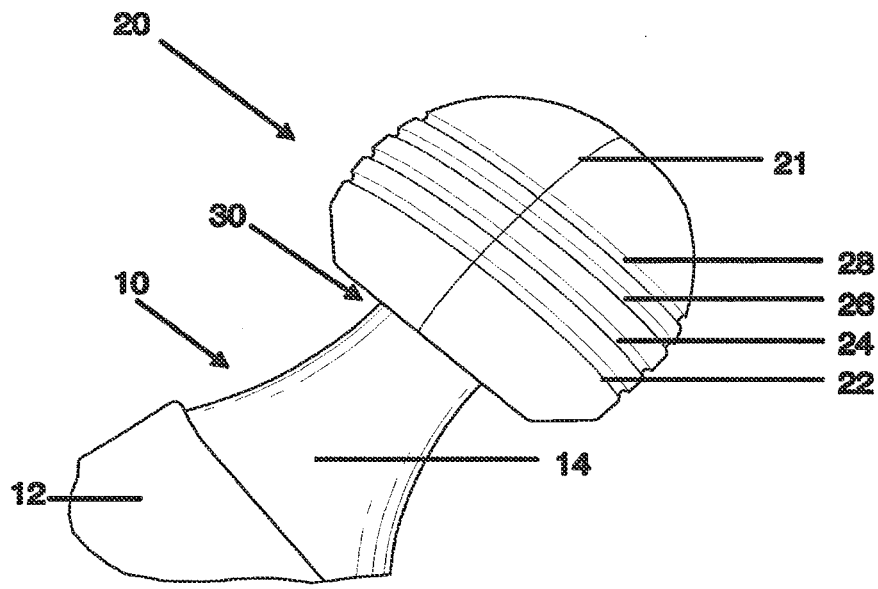
FIG. 2 illustrates a trial femoral head according to some embodiments of the present invention.

FIG. 2 illustrates a femoral head (20) according to some embodiments of the present invention. Femoral head (20) may be an implant, or trial that may be disposable. Femoral head (20) is placed on a femoral neck (14) of a femoral stem, broach, or other femoral component (12) and is held thereto by means for connecting (30). Means for connecting may comprise for instance, a frictional taper fit, spline, keyed shaft, screw thread or other means known in the connection arts. If desired, femoral head (20) and femoral neck (14) could be combined as one unit and adapted to connect to the femoral stem, broach, or other femoral component (12). Femoral head (20) employs indicia (21,22,24,26,28). The indicia may be provided to any visible outer surface portion of the femoral head (20), but is preferably provided to at least a portion of an articulating surface. In the embodiment illustrated in FIG. 2, the indicia comprises a series of colored bands (22,24,26,28), each band being configured to indicate an orientation of an acetabular component with which it articulates. For instance as shown, indicia may comprise one or more optional read lines (21) to indicate the location where a reading is to be taken. Indicia may further comprise a series of latitude lines to indicate amount of abduction/adduction of an acetabular component. As shown, the series of colored bands (22,24,26, 28) may be flush with the articulating surface or provided as recessed grooves as shown. One of the bands (22,24,26,28) may represent a "target" or "neutral" band line (24). When the femoral head (20) is placed within an acetabular component, and when the patient's leg is oriented in a predetermined position, and when an inner rim or edge portion of the acetabular component borders the neutral band line (24), a surgeon will know that the acetabular component has been installed into the pelvic bone correctly with an approximate 45 degrees of abduction. If an inner rim or edge portion of the acetabular component borders band line (22), a surgeon will be notified that the acetabular component has been installed into the pelvic bone with slightly more abduction than 45 degrees, for example, 60 degrees. If an inner rim or edge portion of the acetabular component borders band line (26), a surgeon will be notified that the acetabular component has been installed into the pelvic bone with slightly less abduction than 45 degrees, for example, 30 degrees. Warning bands (28) may be advantageously employed to indicate that an acetabular component is too vertical, which could increase the risk of dislocation and/or impingement. In these cases, a surgeon may consider removing the previously installed acetabular component, repositioning the acetabular component based on the information received by the indicia, re-implanting the acetabular component, and then performing a second trial reduction to ensure that the acetabular component has been repositioned with a correct abduction angle.

It should be recognized that the number, graduation, color, and spacing between bands may be varied to obtain different indications. Indicia may be modified in any manner which is most convenient to a user or manufacturer. For instance, the neutral band line (24) may indicate an abduction angle of 40 degrees instead of 45 degrees. In another instance, band line

(26) may indicate an acetabular component that is oriented roughly 10 degrees further in adduction than the desired neutral band line (24) (instead of 15 degrees). It should also be appreciated that the acetabular components used with the femoral head (20) of the present embodiment may be employed with markings or other indicia to aid in reading the indicia (21,22,24,26,28) located on the femoral head (20). Moreover, read points may comprise an inner rim portion of an acetabular liner, an outside portion of an acetabular shell component, or a separate jig or fixture which temporarily extends from a trial liner or acetabular shell component and serves as a pointer (e.g., removable pointer).

Figure 3:
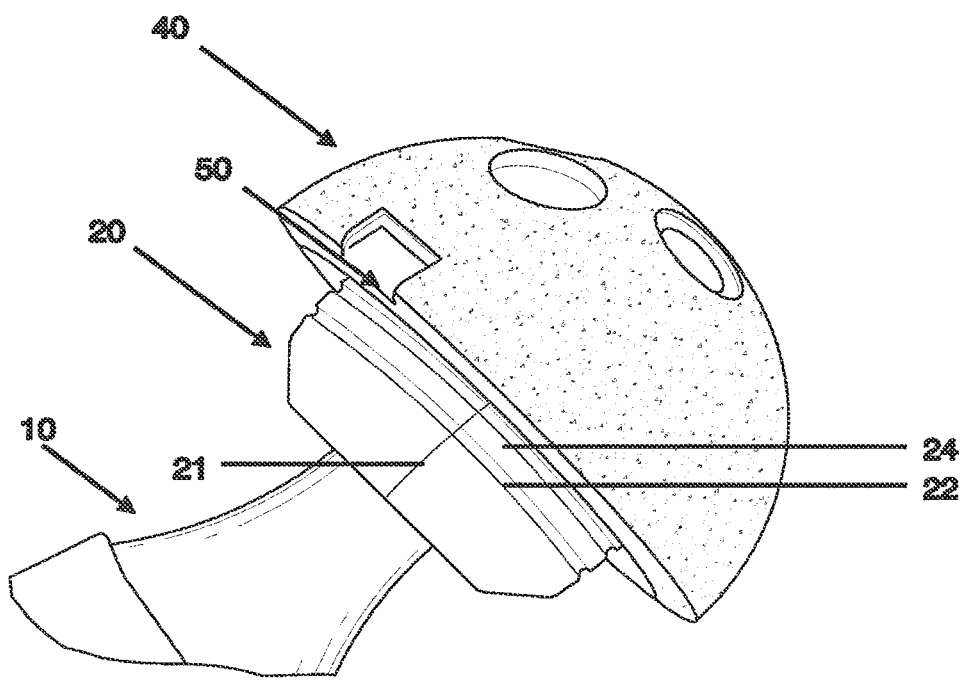
FIG. 3 illustrates the trial femoral head of FIG. 2 coupled with a correctly aligned acetabular shell component and liner, in a neutral leg position.

FIG. 3 illustrates a femoral head (20) as shown in FIG. 2, articulating with at least one acetabular shell component, when a patient's leg is positioned in a predetermined "neutral" position. The acetabular component shown comprises an acetabular shell component (40) and an acetabular liner component (50). In some cases, a desirable neutral leg position may be at full resting extension and internally rotated by an amount equal to the natural femoral neck version of the patient or implant (e.g., about 15 degrees). However, this predetermined "neutral" leg position may vary and the indicia may vary correspondingly. As shown in FIG. 3, the acetabular component is shown to be correctly oriented in its proper amount of abduction and anteversion (i.e., generally 45 degrees abducted and 20 degrees anteverted). The neutral band line (24) borders an inner rim of the acetabular component.

Figure 4:
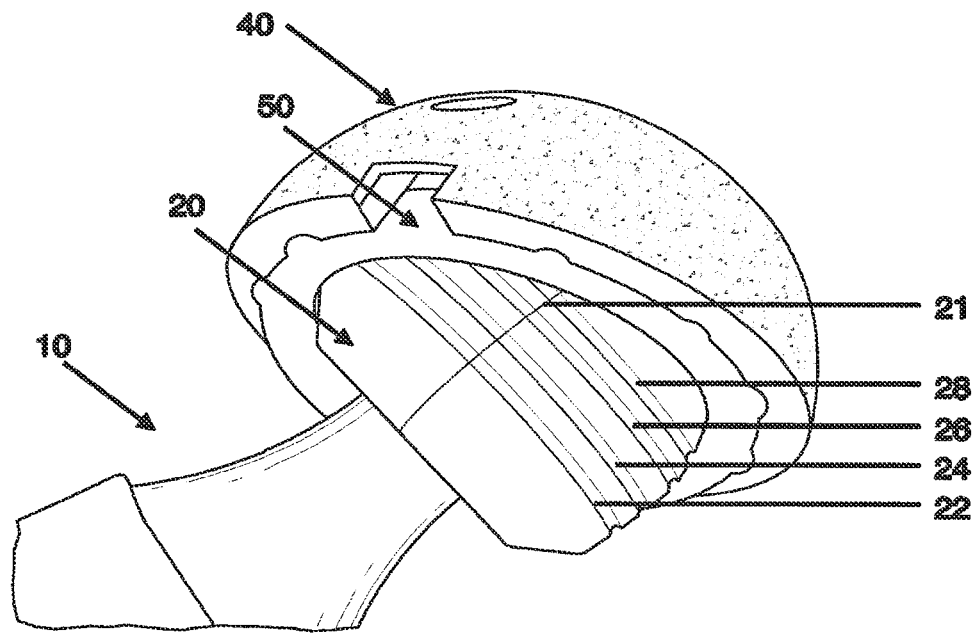
FIG. 4 illustrates the trial femoral head of FIG. 2 coupled with a grossly anteverted and adducted acetabular shell component and liner, in a neutral leg position.

FIG. 4 illustrates one example of a malpositioned acetabular component when a patient's leg is positioned in a predetermined "neutral" position. An inner rim of the acetabular liner component (50) adjacent the read line (21) on the femoral head (20) is proximate a warning band (28). In such a case, a surgeon would be informed that the acetabular component has been installed into the pelvic bone at too much of a vertical angle with very little (e.g., 15 degrees) abduction. A decision to remove and re-install the acetabular component will be made easier with the indicia. Moreover, due to the nature that a rim portion of the acetabular liner component (50) is not parallel to bands (22,24,26,28), a surgeon may also realize that the acetabular components (40,50) are oriented too far anteverted. This information may be useful during the step of repositioning of the acetabular shell component (40), since the surgeon will be able to correct both version and abduction in only one removal step.

Figure 5:
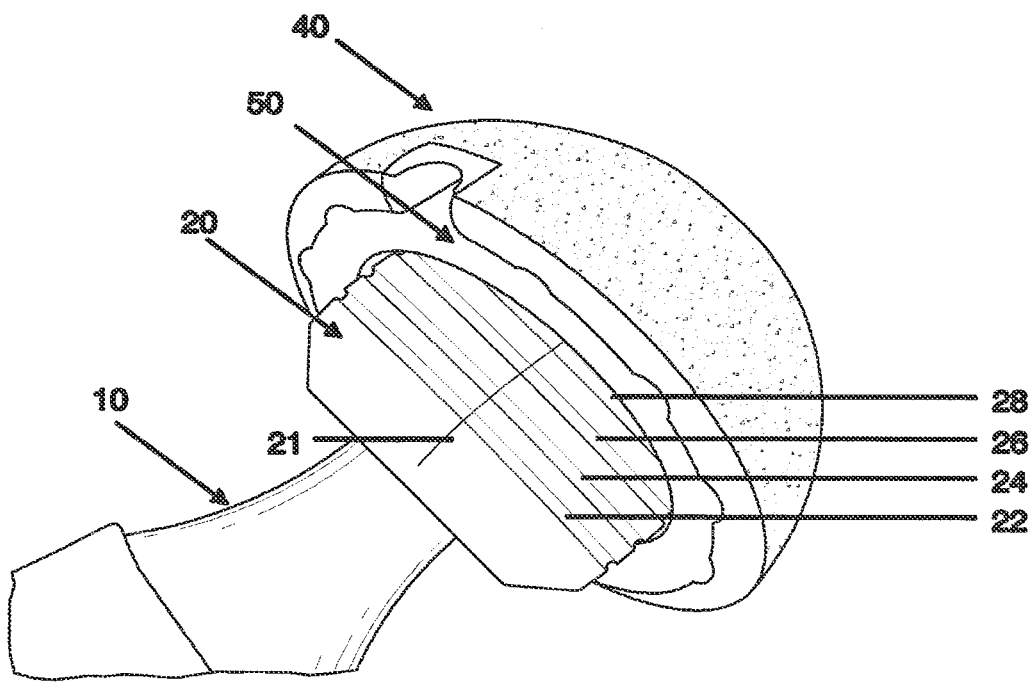
FIG. 5 illustrates the trial femoral head of FIG. 2 coupled with an acetabular shell component and liner too far in adduction, in a neutral leg position.

FIG. 5 illustrates another example of a malpositioned acetabular component when a patient's leg is positioned in a predetermined "neutral" position. An inner rim of the acetabular liner component (50) adjacent the read line (21) on the femoral head (20) is proximate a warning band (28). In such a case, a surgeon would be informed that the acetabular component has been installed into the pelvic bone at too much of a vertical angle with very little (e.g., 15 degrees) abduction. A decision to remove and re-install the acetabular component will be made easier with the indicia provided on the femoral head (20). Since it appears in FIG. 5 that a rim portion of the acetabular liner component (50) is generally parallel with each of the band lines (22,24,26,28), a surgeon may realize that the acetabular shell component (40) has been installed with the proper amount of anteversion, and only needs adjustment in the coronal plane, that is, the acetabular shell component (40) only needs to be anteverted. In a case where the distance between each band represents 15 degrees of version, FIG. 5 would suggest that the acetabular components need to be anteverted roughly 30 degrees to be properly oriented at 45 degrees in abduction.

Figure 6:
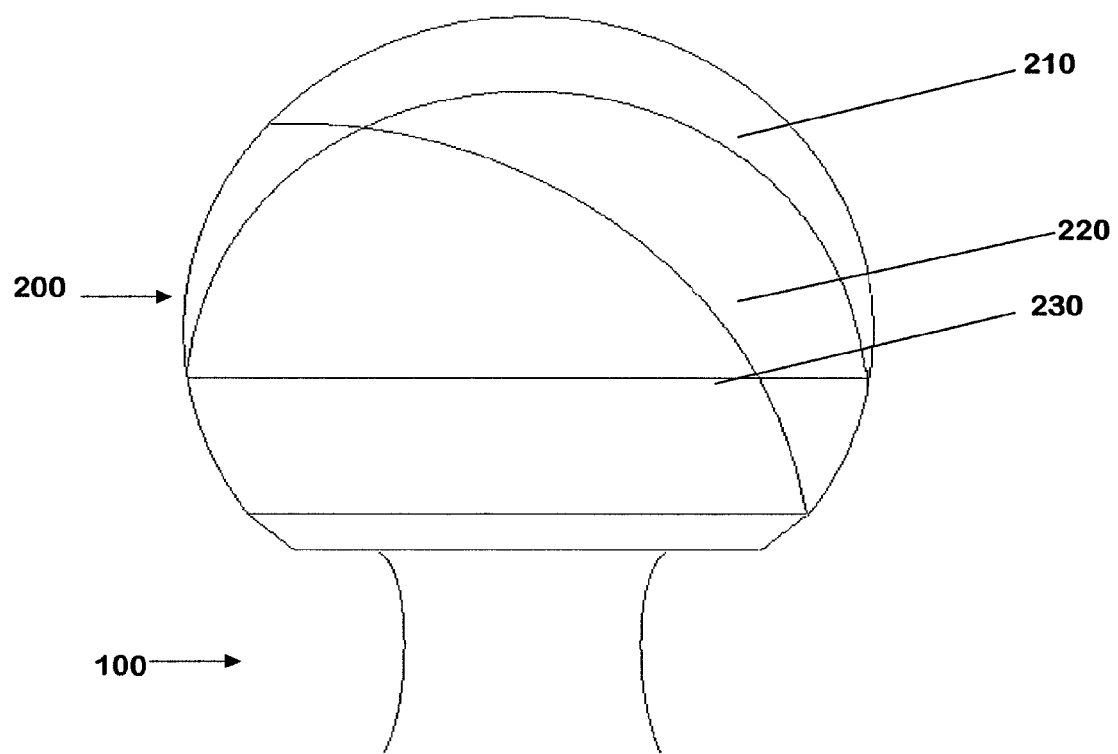
FIG. 6 is a 2-D schematic diagram of femoral head indicia according to some embodiments of the present invention.

FIG. 6 illustrates femoral head indicia according to other embodiments of the present invention. A femoral head (200) is placed on a femoral neck (100). Femoral head (200) has indicia thereon, the indicia comprising one or more line markings (210,220,230). A first line marking (210) may be employed, the first line marking (210) indicating an acetabular component orientation of zero degrees abduction and zero degrees anteversion relative to the axes of the body shown in FIG. 1. In other words, when a patient's leg is positioned in a predetermined "neutral" position, and the femoral head (200) is positioned within an acetabular component (not shown), an inner rim of the acetabular component (not shown) would align and border the first line marking (210) if the acetabular component is oriented with zero degrees abduction and zero degrees anteversion. A second line marking (220) may be employed to indicate an acetabular component orientation of zero degrees of abduction and the maximum amount of anteversion possible before impingement occurs, when a patient is in the predetermined "neutral" position. A third line marking (230) may be provided to indicate an acetabular component orientation of 45 degrees abduction and zero degrees of anteversion. Other line markings may be used to represent other scenarios.

FIGS. 7a and 7b illustrate two of many preferred embodiments of the present invention. A femoral head (200) adapted for cooperation with a femoral neck or stem (100) is provided. Femoral head (200) may be a trial component or a permanent implant. Femoral head (20) has indicia thereon, the indicia comprising at least one color body (240,242,244). Color bodies (240,242,244) may comprise colored, non-colored, whitespace, shaded, crosshatched or other means for visually separating areas of the femoral head (200), and may be provided to the femoral head (200) in any conventional manner including but not limited to: ceramic glazes, annodization, colored inserts, stickers, markers, powder coating, overmoulded colored plastics, etc. In the embodiment shown in FIGS. 7a and 7b, an abduction color body (240) may be used to indicate that an acetabular component is not positioned far enough in abduction (or otherwise less than a predetermined angle). An anteversion color body (242) may be used to indicate that an acetabular component is not anteverted far enough (or otherwise less than a predetermined angle). Color body (244) may comprise whitespace or the natural color of the femoral head trial (20). In use, a surgeon re-locates the femoral head (200) into an acetabular component (not shown). The patient's leg is then placed in a predetermined "neutral" position. If only color body (244) is visible, it may mean that the surgeon has correctly installed an acetabular component with, for example, at least 45 degrees of abduction and for example, at least 25 degrees of anteversion. Alternatively, if only color bodies (244) and (242) are visible when a patient's leg is placed in a "neutral" position, it may be possible that the acetabular component (not shown) is oriented with not enough anteversion (e.g., less than 25 degrees of anteversion, for example). Even more alternatively, if all color bodies (240,242,244) are visible when a patient's leg is placed in a "neutral" position, it may be possible that the acetabular component (not shown) is oriented with not enough anteversion and not enough abduction (e.g., less than 25 degrees of anteversion and less than 45 degrees of abduction, for example).

Since patient demands vary, it may be desirable to permanently orient an acetabular component with less anteversion and less abduction. In such cases, it may be desirable to add a plurality of additional markings to the indicia on the femoral head (200) to precisely determine an offset from the neutral line. Some of the additional markings may comprise one or more anteversion markings (246) which, when a rim portion of an acetabular component is aligned with, circumferentially borders, or is parallel with the one or more anteversion markings (246), it may indicate that the anteversion angle of the acetabular component is proper (e.g., 25 degrees), but the abduction angle of the acetabular component is not proper (e.g., too far in adduction). Likewise, additional markings may include one or more abduction markings (247) which, when a rim portion of an acetabular component is aligned with, circumferentially borders, or is parallel with the one or more abduction markings (247), may indicate that the abduction angle of the acetabular component is proper (e.g., 45 degrees), but the anteversion angle of the acetabular component is not proper (e.g., too far in anteversion). The markings illustrated in FIGS. 7a and 7b are examples only, and in no way intend to limit the invention to what is shown.

Figure 7:
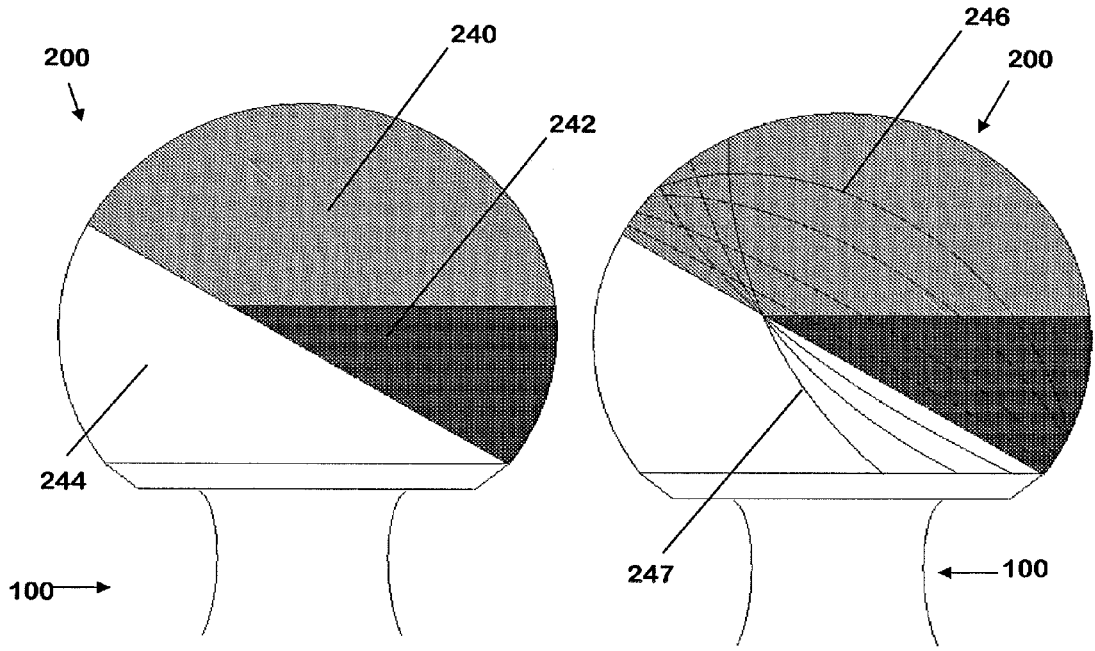
FIGS. 7a and 7b are 2-D schematic diagrams representing femoral head indicia according to some embodiments of the present invention.
Figure 8:
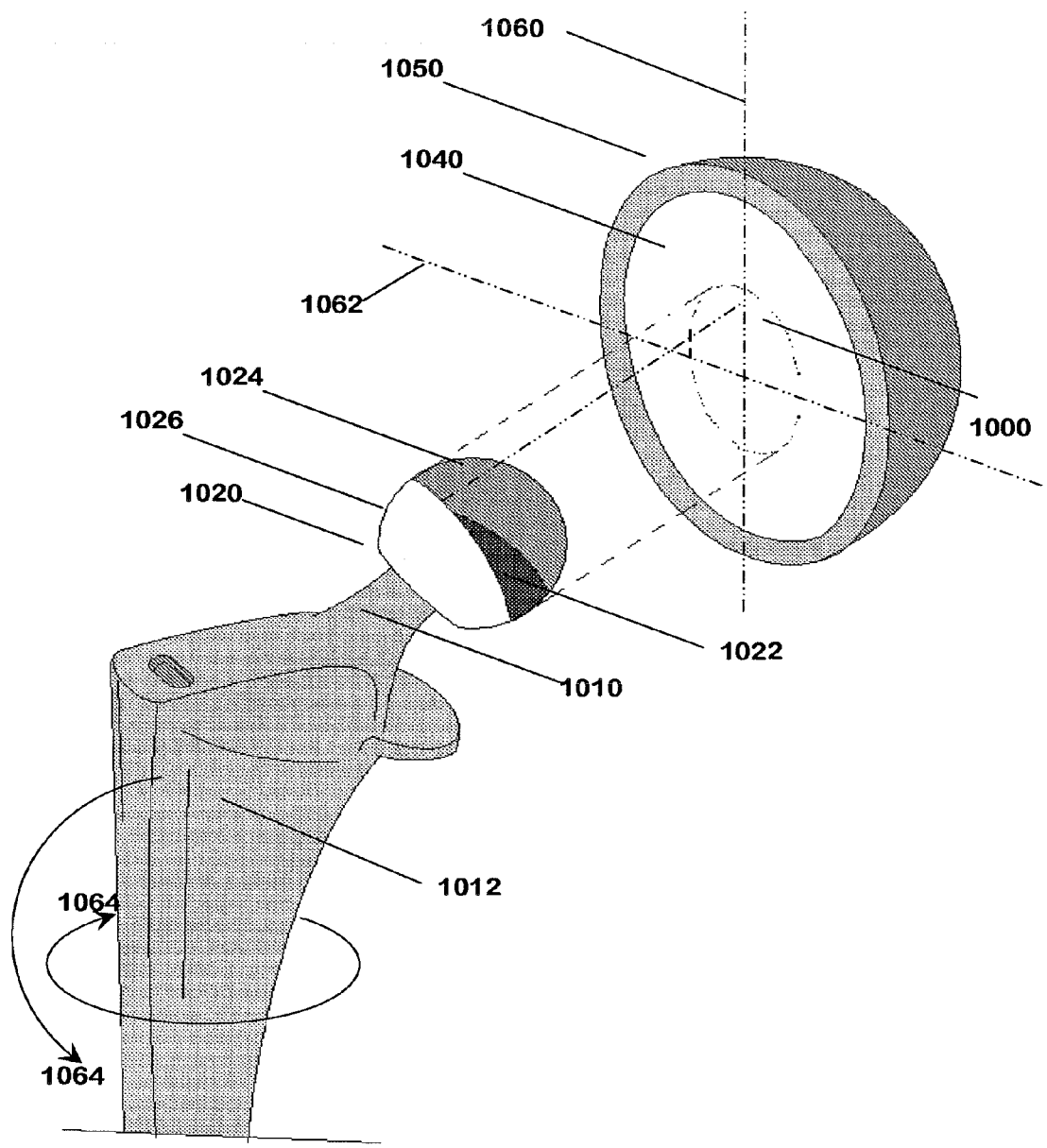
FIG. 8 illustrates a method of determining a spatial orientation of an acetabular prosthesis according to some embodiments of the present invention.

FIG. 8 illustrates a femoral head according to the embodiment shown in FIG. 7a. Femoral head (1020) is placed onto a femoral neck (1010) of a femoral stem component (1012). Femoral head (1020) has indicia thereon, the indicia comprising three color bodies (1022,1024,1026). Femoral head (1020) may be a trial femoral head which is placed into a liner (1040) and allowed to articulate therewith. Liner (1040) may be a trial liner placed into an acetabular shell component (1050) which has been installed into a prepared acetabulum, the acetabular shell component (1050) having a vertical axis (1060) and a horizontal axis (1062). During trial reduction, a patient's leg is moved into a predetermined "neutral" leg position. The predetermined "neutral" leg position may be, for instance, but not limited to full relaxed extension at zero degrees abduction, zero degrees anteversion, and approximately 15 degrees internal rotation or otherwise, internally rotated by an amount equal to the amount of version of the natural or artificial femoral neck. While in the predetermined "neutral" leg position, if only color body (1026) is visible to the surgeon, there is a good possibility that the acetabular shell component (1050) has been installed with at least a predetermined amount of anteversion and abduction (e.g., at least 20 and 45 degrees, respectively). If color bodies (1026) and (1022) are visible to the surgeon in the predetermined "neutral" position, there may be a possibility that the acetabular shell component (1050) has been installed with not enough anteversion, and a sufficient amount (e.g., equal or greater than 45 degrees) of abduction. If all three color bodies (1022,1024,1026) are visible to the surgeon in the predetermined "neutral" position, there may be a possibility that the acetabular shell component (1050) has been installed with an insufficient amount of anteversion (e.g., less than 20 degrees), and also an insufficient amount (e.g., less than 45 degrees) of abduction.

If only a slight amount of color from bodies (1024) and (1022) is visible to the surgeon around the inner rim (1000) of the liner (1040) while the patient is in the predetermined "neutral" position, the surgeon may decide that the orientation of the acetabular shell component (1050) and liner (1040) is acceptable and proceed with implantation without removing and repositioning the component (1050).

Figure 9A:
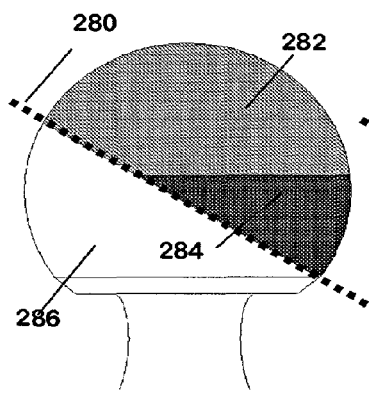
FIGS. 9a-f illustrate several examples of how to reading femoral head indicia according to some embodiments of the present invention.

FIGS. 9a-f illustrate several scenarios which might occur when using the present invention, particularly with the embodiments shown in FIGS. 7a-8. Line (280) represents an inner or outer rim or edge of an acetabular component, which may be for instance, an inner rim of an acetabular shell component, cup, or liner. Indicia is located on a femoral head, the indicia comprising a first body area (286), a second body area (284), and a third body area (282). Referring to FIG. 9a, a surgeon will typically read line (280) only when a patient's leg is in a predetermined "neutral" position. The second body area (284) relates to anteversion angle and the third body area (282) is related to abduction angle.

According to FIGS. 9a-9f, the acetabular component may need to be oriented slightly more in abduction if the third body area (282) is visible. Additionally, the acetabular component may need to be oriented slightly more in anteversion if the second body area (284) is visible. However, according to FIG. 9a, since line (280) is generally parallel to a neutral line shared by all of first (286), second (284), and third (282) bodies, a surgeon may decide to proceed with surgery since this generally means that anteversion angle is okay and abduction angle is the only angle which is lightly less than desired.

Figure 9B:
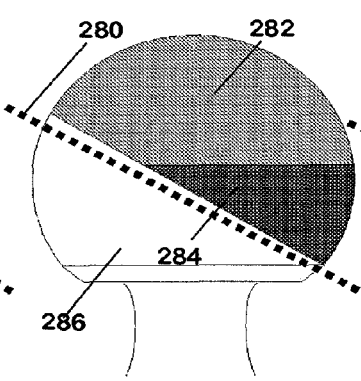

According to FIG. 9b, line (280) is aligned with and borders a neutral line on the femoral head. Therefore, it may be assumed that the acetabular component is well-aligned to a predetermined orientation (e.g., 20 degrees anteversion and 45 degrees abduction).

Figure 9C:
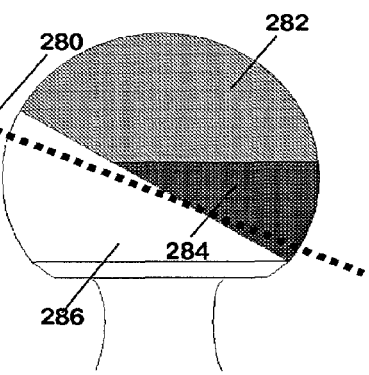

FIG. 9c might suggest that the abduction angle of the acetabular component (not shown) is correct; however, the acetabular component is slightly more anteverted than a predetermined amount (e.g., 25 degrees). Since the second body area (284) is visible to the surgeon, and the third body area (282) is not visible to the surgeon, it may be possible that the acetabular shell component needs only to be retroverted slightly or that the observed angle is acceptable.

Figure 9D:
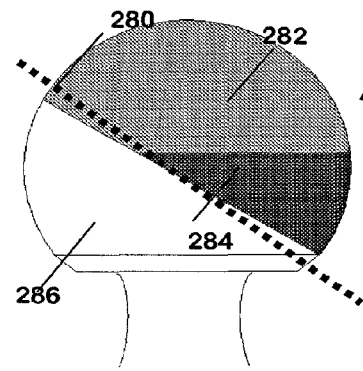
Figure 9E:
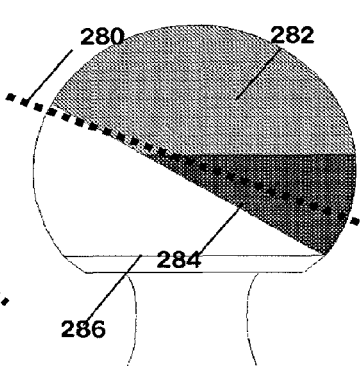
Figure 9F:
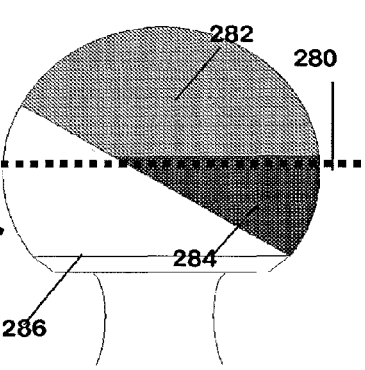

FIG. 9d might suggest that an acetabular component has been installed with a slightly less-than-ideal anteversion angle, and slightly more-than-ideal abduction angle. FIG. 9e might suggest that an acetabular component has been oriented with too much anteversion and too little of an abduction angle. FIG. 9f might suggest that an acetabular component has been oriented with no anteversion angle, and with slightly less abduction than ideal.

It is anticipated that many more situations are possible than those represented in FIGS. 9a-9f. It should be noted that indicia serve only as a means to inform and guide a surgeon, and that all actual intraoperative decisions to remove and reposition a well-fixed acetabular component based on the indicia is to the sole discretion of the surgeon.

Figures 10A, 10B:
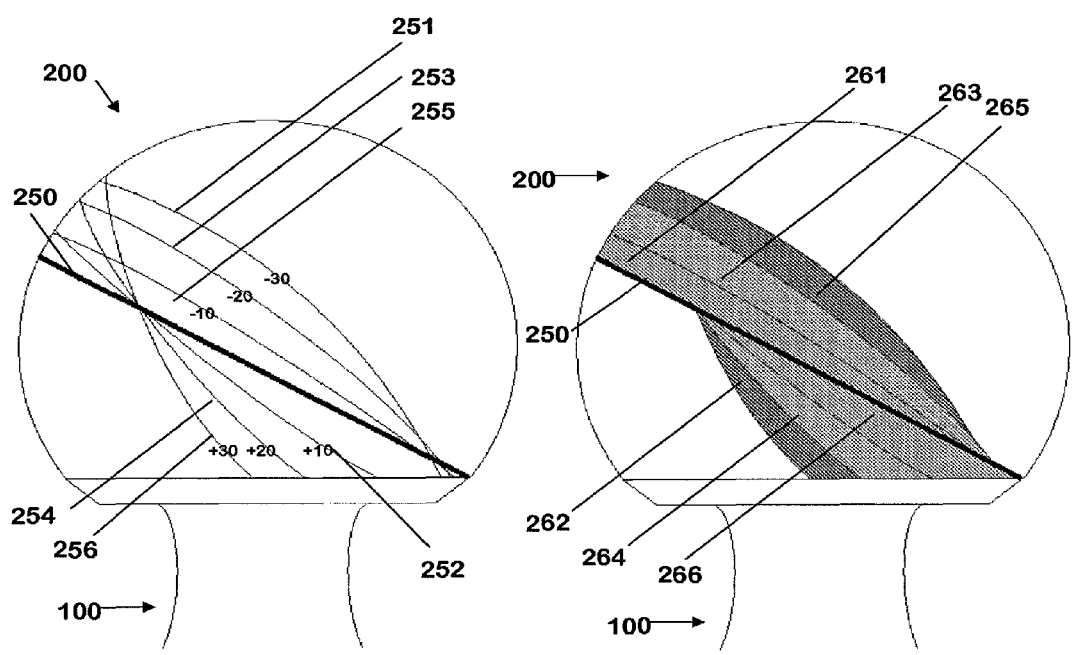
FIGS. 10a and 10b are 2-D schematic diagrams representing femoral head indicia according to some embodiments of the present invention.

FIG. 10a illustrates a femoral head (200) comprising indicia according to some embodiments of the present invention. Indicia may comprise a "target" or "neutral" line (250), which indicates a predetermined position of an acetabular component when a patient's leg is placed in a predetermined "neutral" position. Indicia may further comprise spaced anteversion markings (252,254,256) each indicating a specified number of degrees of anteversion from the neutral line (250). The anteversion markings (252,254,256) may be provided with alpha-numeric symbols or characters to indicate specific quantitative amounts of deviation from the neutral line (250). Likewise, abduction markings (251,253,255) may be employed, each indicating a specified number of degrees of retroversion from the neutral line (250). The abduction markings (251,253,255) may be provided with alpha-numeric symbols or characters to indicate specific quantitative amounts of deviation from the neutral line (250).

FIG. 10b illustrates an alternative embodiment to the one shown in FIG. 10a. Rather than using anteversion and abduction markings (251,252,253,254,255,256) and/or the alphanumeric symbols or characters shown in FIG. 10a, indicia may comprise a series of colored bands on a femoral head (200). Each colored band may be categorized into one or more bands of different confidence levels. Colored bands (266,261) having good confidence levels may be colored green and be located most adjacent a neutral line (250); the neutral line identifying the ideal or desired acetabular component orientation. For instance, if an inner rim or edge of an acetabular liner borders or rests within the lower green anteversion band (266), it may suggest that the acetabular liner is in an ideal or very close to ideal spatial orientation regarding anteversion. Likewise, if an inner rim or edge of an acetabular liner borders or rests within the upper green abduction band (261), it may suggest that the acetabular liner is positioned in an ideal or very close to ideal spatial orientation with regard to abduction. As spatial orientation of an acetabular component deviates from the "target" or "neutral" line (250), an inner rim or edge of an acetabular liner may border or rest within abduction and/or anteversion bands of colors other than green. For instance, if an inner edge or rim of an acetabular liner borders or rests within an orange-colored abduction band (263) and a red-colored anteversion band (262), a surgeon may want to relocate the position of the acetabular component because it is moderately retroverted and severely anteverted. In another instance, if an inner edge or rim of an acetabular liner borders or rests within a green-colored abduction band (261) and an orange-colored anteversion band (264), a surgeon may decide that the abduction angle of the acetabular component is ideal; and while the acetabular component is moderately over-anteverted, he/she may wish to leave a well-fixed acetabular component in-situ rather than removing it and relocating it in slight retroversion.

Figure 11:
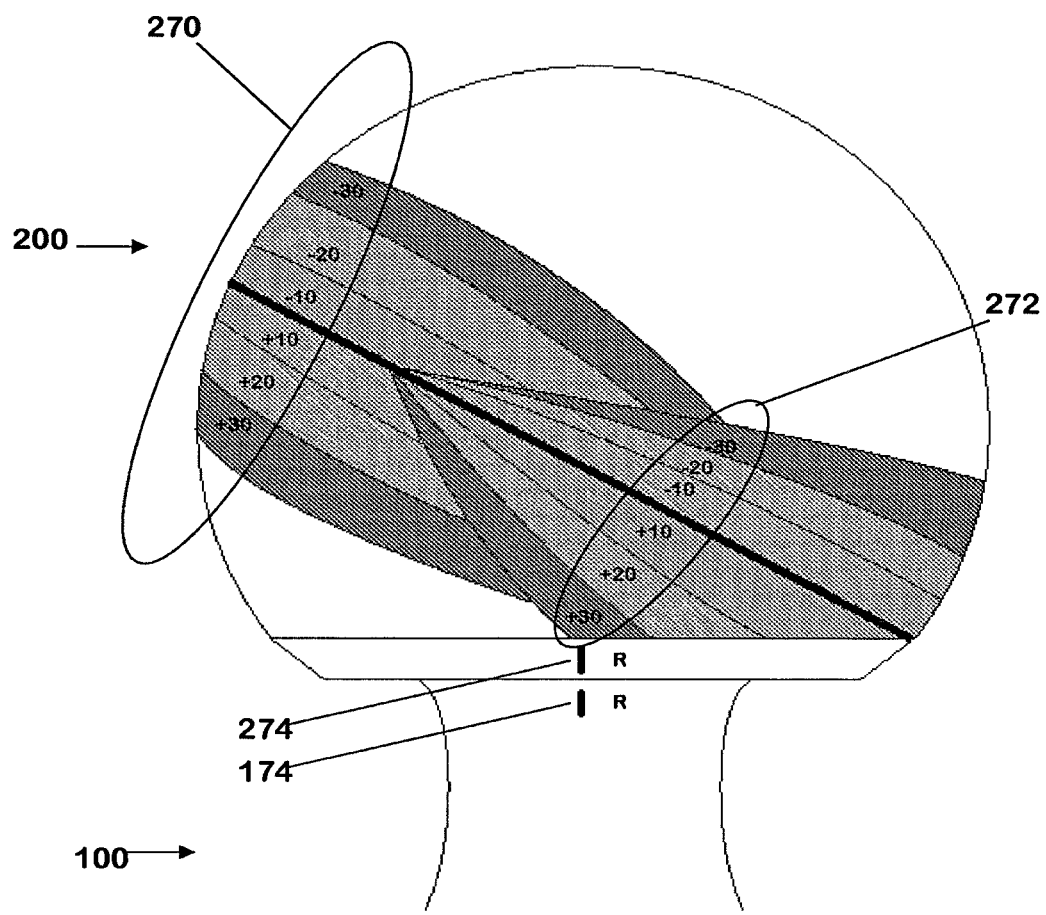
FIG. 11 is a 2-D schematic diagram of femoral head indicia according to some embodiments of the present invention.

FIG. 11 illustrates a femoral head having thereon, indicia according to yet other embodiments of the present invention. The indicia shown is similar to indicia found in FIG. 10b; however, the indicia further comprises means for indicating abduction and version angles both above and below the neutral line. For instance a surgeon may read abduction angle from area (270) and read anteversion angles from area (272).

In order for some embodiments of the present invention to work properly, a femoral head (200) having eccentric, non-concentric, or otherwise non-symmetrical indicia thereon (as is shown in FIG. 11 and others) should be oriented onto a femoral neck or stem (100) properly. In such cases, keying may be employed to control radial positioning of the femoral head (200) onto the femoral neck or stem (100). Alternative to keying, indicia may comprise radial alignment markings (174,274) or equivalent means on both the head (200) and the femoral neck or stem (100). If the same femoral head (200) is to be used for both left and right hip arthroplasty (e.g., a trial femoral head 200 having right hip indicia on one side and left hip indicia on its opposing side), it may be desirable to place alpha-numeric identifiers adjacent to the radial alignment markings (174,274) in order to ensure correct radial orientation of the femoral head (200) on the femoral neck or stem (100). For example, for a right hip, a surgeon may align a double-sided femoral trial head (200) such that its alignment mark (274) having an "R" next to it is aligned with an alignment mark (174) on the femoral neck or stem (100). Alignment marks (274) may be situated so that they face superiorly, most lateral, most distal, or such that they align with a longitudinal or transverse axis of the femoral neck or stem (100). It should be understood that the concept of correctly radially-orienting the femoral head (200) onto a femoral implant, broach, or trial stem (100) is in no way limited to only what is disclosed. Rather, multiple means for ensuring correct relative angular positioning will become obvious from this disclosure.

Figure 12:
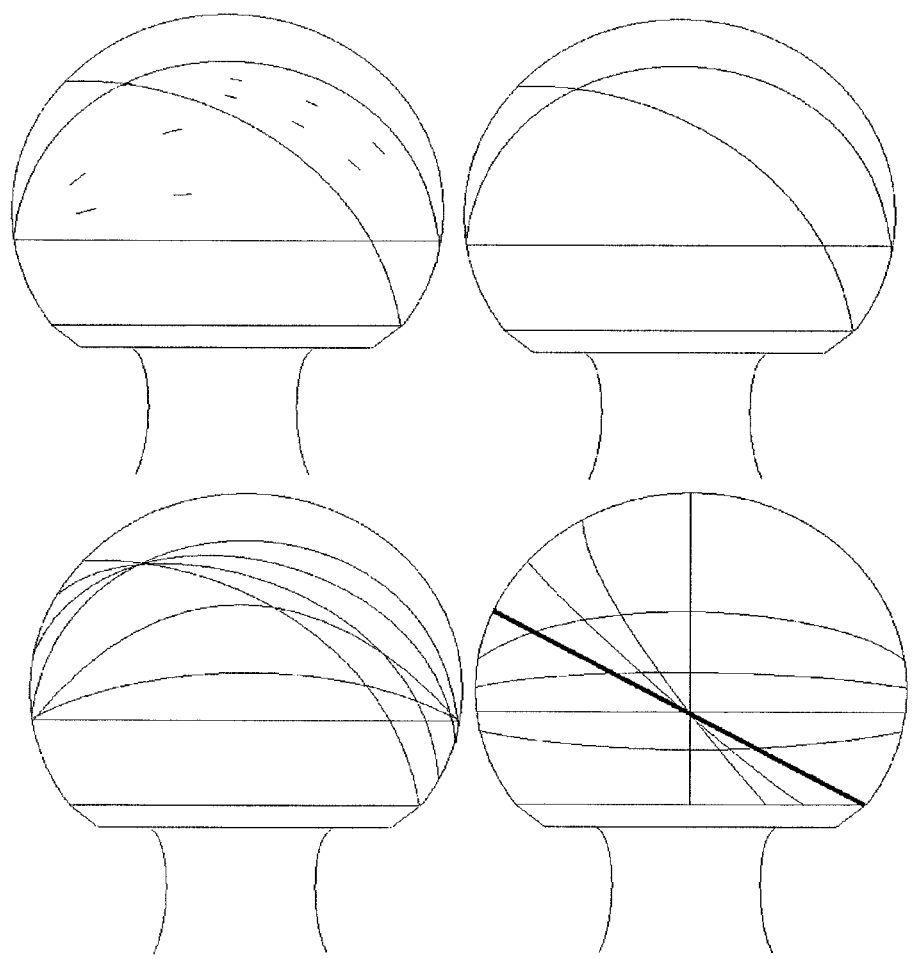
FIG. 12 shows several non-limiting alternative schematic diagrams of femoral head indicia according to some embodiments of the present invention.

FIG. 12 illustrates several other non-limiting embodiments of sample indicia within the scope of the present invention.

Figures 13A, 13B, 13C, 13D, 13E, 13F:
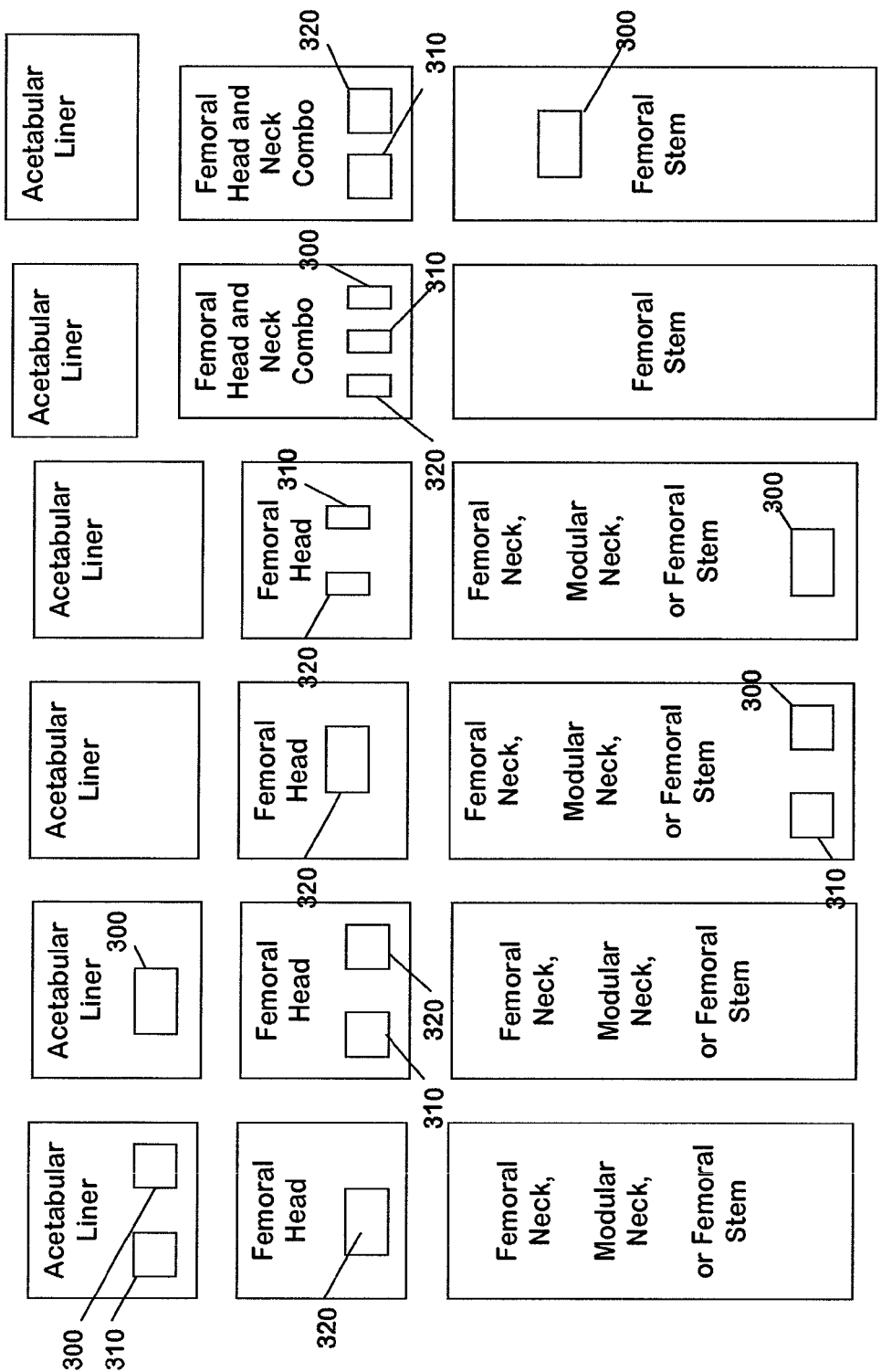
FIGS. 13a-f illustrate several apparatus for internally illuminating indicia according to some embodiments of the present invention.

FIGS. 13a-f illustrate several means for backlighting the indicia of the present invention for improved visualization during surgery. As previously discussed in this disclosure, a means for illumination (300) may illuminate indicia (320) via a means for channeling illumination (310). Means for illumination (300) may comprise, but is not limited to: a light source, a filament, a bulb, a light-emitting diode (LED), and/or phospholuminescent materials. Illumination may be directed through trialing components using means for channeling illumination (310), the means for channeling illumination comprising transparent/translucent materials, fiber optic components, fiber optic cables, lenses, reflective surfaces, mirrors, etc. The means for illumination and the means for channeling illumination may be located on or within any of the aforementioned medical implants or trial implants as shown in the figures. FIG. 13a suggests a means for illumination (300) and a means for channeling the illumination (310) both located on or within a trial acetabular liner, such that indicia (320) located on or within a femoral head may be easily viewed. Alternatively, FIG. 13b suggests a means for illumination (300) located on or within a trial acetabular liner, and both a means for channeling the illumination (310) and indicia (320) located on or within a femoral head. Even more alternatively, FIG. 13c suggests both a means for illumination (300) and a means for channeling the illumination (310) located on or within a femoral neck, modular neck, or femoral stem, such that indicia (320) located on or within a femoral head may be easily viewed. FIG. 13d suggests placing a means for illumination (300) on or within a femoral neck, modular neck, or femoral stem, such that indicia (320) located on or within a femoral head may be easily viewed through a means for channeling illumination (310) also located on or within the femoral head. FIG. 13e suggests placing a means for illumination (300), a means for channeling illumination (310), and indicia (320) on or within a femoral head and neck combo for easy backlit viewing when using instrumentation which is designed to perform trials off of a broach or other trial stem left within the femoral canal. FIG. 13f suggests an embodiment similar to the one in 13e, wherein the means for illumination (300) is alternatively placed on or within a femoral stem or broach.

Referring to FIG. 14, indicia (400) according to some embodiments of the present invention may comprise a material which illuminates when subjected to one or more predetermined wavelengths of light (420). Such materials may comprise phospholuminescent dyes, pigments, glow-in-the dark materials, etc. which are illuminated in surgery by an external light source (410) as shown in FIG. 14. The materials may still be visible in the absence of an external light source (410) and/or predetermined wavelengths of light (420), but may be configured to glow brighter in the presence of the light source (410) and light (420) produced therefrom.

As described above, mapping may be accomplished through the use of indicia applied to any one of an acetabular component, shell, cup, cage, liner, skirted liner, femoral head, trial neck, trial modular neck, femoral stem, femoral broach, trial femoral resurfacing head, or femoral component. The indicia may comprise, without limitation, markings, alpha-numeric indicia, series of lines, grids, straight lines, shadings, contoured lines, contour envelopes, series of dashed lines, colored bands, changes in texture, ridges, grooves, plateaus, plotted series of dots, recessed colors, color groupings, cross-hatch markings, colored snap rings which fit into annular grooves, colored arrays, etc.

The indicia of some embodiments of the present invention may be backlit for improved visualization during surgery as shown in FIGS. 13a-f. Backlighting of indicia (320) may be facilitated by a means for illumination (300) including but not limited to: a light source, a filament, a bulb, a light-emitting diode (LED), and/or phospholuminescent materials. Illumination may be directed through trialing components using means for channeling illumination (310), the means for channeling illumination comprising transparent/translucent materials, fiber optic components, lenses, reflective surfaces, etc. The means for illumination and the means for channeling illumination may be located on or within any of the aforementioned medical implants or trial implants.

Indicia (400) according to some embodiments of the present invention may comprise a material which illuminates when subjected to one or more predetermined wavelengths of light (420). Such materials may comprise phospholuminescent dyes, pigments, glow-in-the dark materials, etc. which are illuminated in surgery by an external light source (410) as shown in FIG. 14.

During surgery, a surgeon may perform a range-of-motion (ROM) test by internally and externally rotating the leg, moving the leg in abduction/adduction, distracting or subluxing the leg inferiorly, and and/or moving the leg in anteversion and retroversion. Indicia located on a femoral component—preferably a femoral head trial component, generally acts as a means for indicating the orientation of an acetabular component (e.g., shell, liner, or both). The indicia may indicate the spatial positioning of the acetabular component relative to the femoral component, or relative to the pelvic bone, or both.

In some embodiments of the present invention, a femoral trial head is provided in a surgical instrument kit. The femoral trial head may be a permanent instrument or a disposable trial. In use, the femoral trial head is allowed to articulate with a trial or permanent liner in an installed acetabular shell component. The femoral trial head preferably comprises at least one indicator on an articulating or surrounding surface. The at least one indicator will appear and/or disappear on the femoral trial head as a patient's leg is held in different positions. Exposed or covered indicia may signify that certain portions of the femoral head are covered or uncovered by the liner or shell at any given time, in any given leg position. Visible indicators such as lines, markings, color groupings, or alphanumeric symbols may signify that the acetabular is positioned with too much or too little anteversion and/or abduction. Other indicia may indicate higher risk of impingement or dislocation. Indicia may indicate that an acetabular shell is implanted wrong, regardless of the relative position between the femoral trial head and acetabular component.

During a range-of-motion assessment, a surgeon may place a patient's leg in a predetermined position. Colors or other indicia appearing on the femoral head may suggest that at the predetermined position of the leg (i.e., femur), the femoral head is significantly uncovered in one or more areas due to mal-positioning of the acetabular component (e.g. cup or shell). In such instances, an adjustment of the cup may be necessary.

Particular configurations of indicia may differ for outlying patient populations. In such instances, preoperative planning using conventional templating methods, computerized tomography (CT/CAT) scans, magnetic resonance imaging (MRI) scans, ultrasound scans, or other radiography or tomography methods may be necessary to define a patient-specific configuration. The patient-specific configuration may be employed on a patient-specific femoral trial head component described herein.

Specific angles, colors, and configurations may be more preferable for differently-minded surgeons. For instance, some surgeons may have visual impairments or color blindness. Different countries may use different units of measure. Therefore, the particular size and type of indicia used is not necessarily important and various embodiments may become readily apparent by those of ordinary skill in the art from this disclosure. Indicia may suggest for instance, a number of angles, measured distances (e.g., in millimeters or inches), or other means to convey a spatial orientation.

In some embodiments of the present invention, a simple "neutral" line may be employed to indicate proper orientation of an acetabular component relative to a femoral component or to the body. Such a neutral line may be associated with a corresponding leg position. For instance, a neutral line may comprise an annular line on a femoral trial head, such that when a patient's leg is held in full extension and full adduction, and when the neutral line circumferentially borders the inside rim of an acetabular liner, it may be reasonably determined that the acetabular liner is situated with its longitudinal apex axis at roughly 20 degrees of anteversion and 45 degrees of abduction.

In some embodiments of the present invention, a femoral trial component may be provided, the femoral trial component comprising one or more shades or color groupings, such that when a patient's leg is held in neutral abduction and is internally rotated by an amount equal to the femoral neck version (e.g., in most cases 10-20 degrees), shades or color grouping areas will indicate an ideal cup version and abduction position. For instance, if a first shade or color grouping is visible after holding a patient's leg in neutral abduction and internal rotation by an amount equal to the femoral neck version (e.g., 15 degrees), it may suggest that an ideal acetabular shell component orientation is several degrees further in abduction. If a second shade or color grouping area is visible under the same circumstances, it may suggest that an ideal acetabular shell component placement is slightly more anteverted than the position during trial reduction (i.e., the cup is too vertical and should be moved further into abduction). If both of the first and second shades or color groupings show, it may indicate that an ideal acetabular shell component placement is located further in both anteversion and abduction. Moreover, if no shades or color grouping areas are visible in the same leg position, it may suggest that the acetabular shell component is ideally situated, or that the acetabular shell component is too far anteverted and/or is too far in abduction (this may be assessed with a range-of-motion test). In this scenario, two shades or color groupings may be advantageously utilized to provide a simple and easy way to visually determine how close to ideal an acetabular shell component has been placed relative to either the femoral component and/or the pelvic bone.

It should be noted that the aforementioned embodiment is only one of several non-limiting embodiments of the present invention, and serves only to illustrate one of many advantageous uses of the present invention. The following description of the preferred embodiment(s) is merely exemplary in nature and is in no way intended to limit the invention, its application, or uses.

The embodiment provides, in part, a novel method of determining the orientation of an acetabular prosthesis using indicia on a femoral prosthesis, and more particularly to a novel method of using indicia on an articulating surface of a femoral component to determine the relative positioning of an acetabular prosthesis.

While specific to a hip implant, these methods and devices may be useful in other surgical procedures and thus these embodiments are not limited to hip implants. Rather the embodiments as presented herein, with only slight modification, may have useful applicability in knee, shoulder, elbow, spine, finger, wrist, and joints of other portions throughout the human body.

As various modifications could be made to the exemplary embodiments, as described above with reference to the corresponding illustrations, without departing from the scope of the invention, it is intended that all matter contained in the foregoing description and shown in the accompanying drawings shall be interpreted as illustrative rather than limiting. Thus, the breadth and scope of the present invention should not be limited by any of the above-described exemplary embodiments, but should be defined only in accordance with the following claims appended hereto and their equivalents.

A surgeon may have additional "feel-good" indication of acetabular component orientation. A properly oriented acetabular component ensures good femoral head coverage and reduced risk of impingement and dislocation/subluxation. Proper head coverage may further result in additional benefits such as reduced wear due to improved distribution of stress within the joint. The present invention could be applied to existing trial femoral heads without the need for any additional instrumentation. Indicia may double as a means for indicating size, shape, offset, product line, key type, and provide many other inherent uses.

In view of the foregoing, it will be seen that several advantages of the invention may be achieved and attained.

The embodiments were chosen and described in order to best explain the principles of the invention and its practical application to thereby enable others skilled in the art to best utilize the invention in various embodiments and with various modifications as are suited to the particular use contemplated.

As various modifications could be made in the constructions and methods herein described and illustrated without departing from the scope of the invention, it is intended that all matter contained in the foregoing description or shown in the accompanying drawings shall be interpreted as illustrative rather than limiting. Thus, the breadth and scope of the present invention should not be limited by any of the above-described exemplary embodiments, but should be defined only in accordance with the following claims appended hereto and their equivalents.

What is claimed is:

1. A method of orienting a prosthetic femoral implant relative to an acetabulum, comprising:
   implanting a femoral stem of the implant within an intramedullary canal of a femur;
   positioning a femoral head member of the implant at least partially in the acetabulum, the femoral head member including a curved articulating surface and a plurality of indicia on the curved articulating surface; and
   orienting the femoral head member relative to the acetabulum and generally aligning one of the indicia on the curved articulating surface with an alignment feature of the acetabulum or an acetabular member positioned within the acetabulum to signify an orientation of the femoral head member in the acetabulum.

2. The method of claim 1, further comprising implanting the acetabular member in the acetabulum such that the femoral head member is at least partially positioned in the acetabular member; and
   wherein the orienting orients the femoral head member relative to the acetabular member.

3. The method of claim 2, further comprising:
   generally aligning another of the plurality of indicia on the curved articulating surface with the alignment feature to signify an improper orientation of the femoral head member relative to the acetabular member wherein the signified improper orientation is a measure of displacement of the acetabular member from a proper orientation of the femoral head member relative to the acetabular member; and
   adjusting an orientation of the acetabular member in the acetabulum such that the amount of adjustment of the acetabular member corresponds to the measure of displacement.

4. The method of claim 3, wherein the measure of displacement is a measure of angular displacement.

5. The method of claim 3, wherein the adjusting of the orientation of the acetabular member comprises adjusting an abduction/adduction angle of the acetabular member.

6. The method of claim 3, wherein the adjusting of the orientation of the acetabular member comprises adjusting an anteversion/retroversion angle of the acetabular member.

7. The method of claim 1, wherein the plurality of indicia comprises illuminated indicia.

8. The method of claim 1, wherein one of the plurality of indicia located on the curved articulating surface is generally aligned with an anatomic feature of the acetabulum to signify a neutral orientation of the femoral head member in the acetabulum, and wherein another of the plurality of indicia located on the curved articulating surface is generally aligned with an anatomic feature of the acetabulum to signify a relative orientation of the femoral head member as the femoral stem is rotated through its range of motion relative to the acetabulum.

9. The method of claim 1, wherein the alignment feature comprises an anatomic feature of the acetabulum.

10. The method of claim 2, wherein the alignment feature comprises a feature of the acetabular member.

11. The method of claim 10, wherein the alignment feature comprises an annular rim portion of the acetabular member.

12. The method of claim 1, wherein the plurality of indicia comprises a series of multi-colored bands or regions defined on the curved articulating surface of the femoral head member.

13. The method of claim 1, wherein the plurality of indicia comprises a plurality of straight lines.

14. The method of claim 1, wherein the plurality of indicia comprises a plurality contoured lines.

15. The method of claim 1, wherein at least one of the plurality of indicia comprises a straight line and wherein at least one of the plurality of indicia comprises a contoured line.

16. The method of claim 1, wherein the plurality of indicia comprises one or more grooves recessed into the curved articulating surface of the femoral head member.

17. A method of orienting a femoral head member of an implant relative to an acetabular member positioned in the acetabulum, comprising:
   implanting a femoral stem of an implant within an intramedullary canal of a femur;
   inserting an acetabular member in the acetabulum;
   positioning a femoral head member of the implant at least partially in the acetabular member, the femoral head member including a curved articulating surface and a plurality of indicia on the curved articulating surface; and
   orienting the femoral head member relative to the acetabular member and generally aligning one of the indicia on the curved articulating surface with an alignment feature of the acetabular member to signify an orientation of the femoral head member relative to the acetabular member.

18. The method of claim 17, further comprising:
   generally aligning another of the plurality of indicia on the curved articulating surface with the alignment feature to signify an improper orientation of the femoral head member relative to the acetabular member wherein the signified improper orientation is a measure of displacement of the acetabular member from a proper orientation of the femoral head member relative to the acetabular member; and adjusting an orientation of the acetabular member in the acetabulum such that the amount of adjustment of the acetabular member corresponds to the measure of displacement.

19. The method of claim 18, wherein the measure of displacement is a measure of angular displacement.

20. The method of claim 18, wherein the adjusting of the orientation of the acetabular member comprises adjusting at least one of an abduction/adduction angle and an anteversion/retroversion angle of the acetabular member.

21. The method of claim 17, wherein one of the plurality of indicia located on the curved articulating surface is generally aligned with the alignment feature to signify a neutral orientation of the femoral head member in the acetabular member, and wherein another of the plurality of indicia located on the curved articulating surface is generally aligned with the alignment feature to signify a proper orientation of the femoral head member as the femoral stem is rotated through its range of motion relative to the acetabulum.

22. The method of claim 17, wherein the alignment feature comprises an annular rim portion of the acetabular member.

23. The method of claim 17, wherein the plurality of indicia comprises a series of multi-colored bands or regions defined on the curved articulating surface of the femoral head member.

24. The method of claim 17, wherein the plurality of indicia comprises at least one of a plurality of straight lines and a plurality of contoured lines.

25. The method of claim 17, wherein the plurality of indicia comprises one or more grooves recessed into the curved articulating surface of the femoral head member.

* * * * *